United States Patent [19]

Hanaoka et al.

[11] Patent Number: 5,233,110
[45] Date of Patent: Aug. 3, 1993

[54] PROCESS FOR THE PREPARATION OF CYCLOOCTENE

[75] Inventors: Taka-aki Hanaoka; Yoshihiro Sugi; Takehiko Matsuzaki; Kazuhiko Takeuchi; Hironori Arakawa, all of Tsukuba, Japan

[73] Assignee: Agency of Industrial Science & Technology, Tokyo, Japan

[21] Appl. No.: 843,332

[22] Filed: Feb. 28, 1992

[30] Foreign Application Priority Data

Mar. 8, 1991 [JP] Japan .................... 3-69155

[51] Int. Cl.$^5$ .................... C07C 2/76; C07C 13/28
[52] U.S. Cl. .................... 585/360; 585/250; 585/271; 585/273; 585/277
[58] Field of Search .............. 585/360, 250, 271, 273, 585/277

[56] References Cited

PUBLICATIONS

P. T. Dragett et al., J. Organometallic Chem. 135 (1977) C60-C62.
R. Spogliarich et al., J. Organometallic Chem. 240 (1982) pp. 453-459.
J. M. Brown et al., J. Chem. Soc., Chem. Commun. (1984) 915-917.

*Primary Examiner*—Olik Chaudhuri
*Assistant Examiner*—C. Everhart
*Attorney, Agent, or Firm*—Nikaido, Marmelstein, Murray & Oram

[57] ABSTRACT

A process for the preparation of cyclooctene which comprises irradiating 1,5-cyclooctadiene with light in the presence of a photodehydrogenation catalyst, acetone and an alcohol to partially hydrogenate the 1,5-cyclooctadiene.

11 Claims, No Drawings

PROCESS FOR THE PREPARATION OF CYCLOOCTENE

BACKGROUND OF THE INVENTION

The present invention relates to a process for the preparation of cyclooctene by hydrogenating 1,5-cyclooctadiene. More particularly, it relates to a process for the preparation of cyclooctene by partially hydrogenating 1,5-cyclooctadiene photochemically by the use of an alcohol as a hydrogen source.

The inventors of the present invention previously found that the Wilkinson complex (see Japanese Patent Publication No. 59-4406) and rhodium compounds (see Japanese Patent Publication No. 60-329) exhibited a remarkably high photocatalytic dehydrogenation activity on 2-propanol in the air, thus accomplishing the inventions relating to photodehydrogenation catalysts. Further, the inventors advanced their studies to find an efficient process for the preparation of ethylene glycol by irradiating methanol with light in the presence of both acetone and a rhodium complex (see Japanese Patent Publication No. 60-6930). In this process, acetone absorbs the light falling thereon to advance the reaction, i.e., acetone functions as a photosensitizer, so that methanol itself need not absorb the falling light.

The inventors of the present invention have made studies on a process for simultaneously conducting the dehydrogenation of a hydrogen source and the hydrogenation of an unsaturated compound by utilizing such a photodehydrogenation catalyst and have accomplished the present invention.

Cyclooctene which is the product of the present invention is one of the important intermediates for the preparation of synthetic resins by metathesis or oxidative ring opening.

SUMMARY OF THE INVENTION

An object of the present invention is to provide a process for preparing cyclooctene from 1,5-cyclooctadiene.

This object can be attained by irradiating 1,5-cyclooctadiene with light in the presence of a photodehydrogenation catalyst, acetone and an alcohol to thereby hydrogenate the 1,5-cyclooctadiene partially.

DESCRIPTION OF THE PREFERRED EMBODIMENTS

In the present invention, a rhodium complex or a mixture thereof with a transition metal salt is used as a photodehydrogenation catalyst.

The rhodium complex may be any one suitably selected from among known ones, so far as it is soluble in the reaction mixture. Preferred examples thereof include rhodium chloride [$RhCl_3$], hexarhodiumhexadecacarbonyl [$Rh_6(CO)_{16}$] and tetrarhodiumdodecacarbonyl [$Rh_4(CO)_{12}$].

Although the amount of the rhodium complex to be used is not particularly limited, but may be arbitrarily selected depending upon the reaction conditions, it is preferable that the rhodium complex be used in an amount raging from $1 \times 10^{-4}$ to $1 \times 10^{-1}$ mmol per mol of the total amount of the acetone and alcohol used.

The transition metal salt functions as a stabilizer for the rhodium complex and a promoter. An iron, cobalt, nickel, copper or zinc salt is used as the transition metal salt. The salt is generally used as chloride, nitrate or sulfate, though the kind of the salt is not particularly limited, but may be any one so far as the salt is soluble in the reaction system. Although the amount of the transition metal salt used is not particularly limited, but may be arbitrarily selected depending upon the reaction conditions, it is preferable that the salt be used in an amount of 0.05 to 3 mol per mol of the rhodium metal in the rhodium complex.

By using the transition metal salt, the reactivity and selectivity of hydrogenation in the preparation of cyclooctene can be improved, which is supported by the fact that the yield of cyclooctene attained in Example 4 which will be described below is much higher than that attained in Example 1 which will be described below, wherein the Example 1 relates to a case of using a rhodium complex alone as the catalyst, whereas the Example 4 relates to a case of using both a rhodium complex and a transition metal salt as the catalyst.

In the present invention, an alcohol is used as a hydrogen donor. The alcohol to be used in the present invention may be any one which has a hydrogen atom at the α-position relative to the hydroxyl group and the dehydrogenation of which advances when no 1,5-cyclooctadiene is present in the reaction system. Preferred examples of the alcohol include methanol, ethanol, 2-propanol and sec-butanol. Further, the amount of the alcohol to be used may be arbitrarily selected.

In the present invention, acetone absorbs light to function as a photosensitizer. The amount of the acetone to be used may be arbitrarily selected in such a range that the photodehydrogenation catalyst, i.e., a rhodium complex alone or its mixture with a transition metal salt can be dissolved therein. It is preferable that the volume ratio of the acetone to the alcohol be within a range of from 0.05 to 2.

In the irradiation according to the present invention, the white light emitted from a high-pressure mercury lamp is preferably used as the light source, though the light source may be any one emitting ultraviolet light having a wavelength of 400 nm or below. Further, the irradiation apparatus to be used may be suitably selected depending upon the reaction vessel and may be either one with outer light source or one with immersion unit. The irradiation time is not particularly limited, but may be suitably selected depending upon the reaction conditions such as the amount of the raw material used and the kind and intensity of the light source in consideration of the progress of the reaction.

The process of the present invention is conducted by feeding 1,5-cyclooctadiene, an alcohol, acetone and a photodehydrogenation catalyst into a reaction vessel such as an irradiation apparatus with outer light source, bubbling an inert gas through the obtained mixture under stirring for a predetermined time, and irradiating the resulting mixture with light. The bubbling of an inert gas is unnecessary during the irradiation. Alternatively, the process may be conducted by feeding an alochol, acetone and a photodehydrogenation catalyst into a reaction vessel, bubbling an inert gas through the mixture, irradiating the resulting mixture with light to liberate hydrogen from the alcohol and feeding 1,5-cyclooctadiene into the reaction vessel.

The amount of the 1,5-cyclooctadiene to be fed is not particularly limited, but may be selected depending upon the reaction rate, the volume of the reaction vessel, and the kind of the light source.

The inert gas to be used in the present invention includes nitrogen, argon and helium. Although the bubbling time may be arbitrarily selected, sufficient bubbling is generally attained in about 15 minutes. Although the bubbling of an inert gas is not always essential, it is effective in accelerating the reaction.

The reaction is generally conducted at ordinary temperature. Although the reaction may be also conducted, if necessary, at a temperature arbitrarily selected within a range of from 0° C. to the boiling point of the reaction solution, it can be sufficiently conducted near room temperature.

According to the process of the present invention, acetone absorbs the light falling thereon to activate a dehydrogenation catalyst and the activated catalyst serves to dehydrogenate an alcohol to thereby liberate hydrogen, which reduces cyclooctadiene into cyclooctene.

Examples according to the present invention will now be described.

EXAMPLE 1

0.3 ml of 1,5-cyclooctadiene, 32 ml of 2-propanol, 8 ml of acetone and 3 mg of tetrarhodiumdodecacarbonyl [$Rh_4(CO)_{12}$] were fed into a 40-ml quartz cell fitted with a gas buret connected thereto. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. In the irradiation, the rays which were emitted from a 500-W high-pressure mercury lamp set on an irradiation apparatus as an outer light source and passed through a filter UV-25, mfd. by Toshiba Corporation, were used. After the irradiation had been conducted for 4 hours in such a manner, the reaction solution was analyzed by gas chromatography. Cyclooctene was obtained in a yield of 81% with the formation of cyclooctane in a yield of 16%. 2 % of unreacted 1,5-cyclooctadiene remained.

EXAMPLE 2

0.3 ml of 1,5-cyclooctadiene, 32 ml of ethanol, 8 ml of acetone and 3 mg of tetrarhodiumdodecacarbonyl [$Rh_4(CO)_{12}$] were fed into the same quartz cell as that used in the Example 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. In the irradiation, the rays which were emitted from a 500-W high-pressure mercury lamp set on an irradiation apparatus as an outer light source and passed through a filter UV-25, mfd. by Toshiba Corporation, were used. After the irradiation had been conducted for 5 hours in such a manner, the reaction solution was analyzed by gas chromatography. Cyclooctene was obtained in a yield of 88% with the formation of cyclooctane in a yield of 12%. No 1,5-cyclooctadiene was detected by the gas chromatography.

EXAMPLE 3

0.3 ml of 1,5-cyclooctadiene, 32 ml of 2-propanol, 8 ml of acetone and 3 mg of tetrarhodiumdodecacarbonyl [$Rh_4(CO)_{12}$] were fed into the same quartz cell as that used in the Example 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. In the irradiation, the rays which were emitted from a 500-W high-pressure mercury lamp set on an irradiation apparatus as an outer light source and passed through a filter UV-25, mfd. by Toshiba Corporation, were used. After the irradiation had been conducted for 5.5 hours in such a manner, the reaction solution was analyzed by gas chromatography. Cyclooctene was obtained in a yield of 79% with the formation of cyclooctane in a yield of 16%. 5% of unreacted 1,5-cyclooctadiene remained.

EXAMPLE 4

0.3 ml of 1,5-cyclooctadiene, 32 ml of 2propanol, 8 ml of acetone, 0.5 mg of ferric nitrate hydrate and 3 mg of tetrarhodiumdodecacarbonyl [$Rh_4(CO)_{12}$] were fed into the same quartz cell as that used in the Example 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. The rays which were emitted from a 500-W high-pressure mercury lamp set on an irradiation apapratus as an outer light source and passed through a filter UV-25, mfd. by Toshiba Corporation, were used in the irradiation. After the irradiation was conducted for 5 hours in such a manner, the reaction solution was analyzed by gas chromatography. Cyclooctene was obtained in a yield of 95% with the formation of cyclooctane in a yield of 5%. No unreacted 1,5-cyclooctadiene was detected by the gas chromatography.

EXAMPLE 5

0.3 ml of 1,5-cyclooctadiene, 32 ml of 2-propanol, 8 ml of acetone, 1.5 mg of ferric nitrate hydrate and 3 mg of tetrarhodiumdodecacarbonyl [$Rh_4(CO)_{12}$] were fed into the same quartz cell as that used in the Exampel 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. The rays which were emitted from a 500-W high-pressure mercuty lamp set on an irradiation apparatus as an outer light source and passed through a filter UV-25, mfd. by Toshiba Corporation, were used in the irradiation. After the irradiation had been conducted for 5 hours in such a manner, the reaction solution was analyzed by gas chromatography. Cyclooctene was obtained in a yield of 95% with the formation of cyclooctane in a yield of 1%. 4% of unreacted 1,5-cyclooctadiene remained.

EXAMPLE 6

0.3 ml of 1,5-cyclooctadiene, 32 ml of 2-propanol, 8 ml of acetone, 2.2 mg of nickel nitrate hydrate and 3 mg of tetrarhodiumdodecacarbonyl [$Rh_4(CO)_{12}$] were fed into the same quartz cell as that used in the Example 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. The rays which were emitted from a 500-W high-pressure mercury lamp set on an irradiation apparatus as an outer light source and passed through a filter UV-25, mfd. by Toshiba Corporation, were used in the irradiation. After the irradiation had been conducted for 5 hours in such a manner, the reaction solution was analyzed by gas chromatography. Cyclooctene was obtained in a yield of 93% with the formation cyclooctane in a yield of 3%. 4% of unreacted 1,5-cyclooctadiene remained.

EXAMPLE 7

0.3 ml of 1,5-cyclooctadiene, 32 ml of 2-propanol, 8 ml of acetone, 1.8 mg of cupric nitrate hydrate and 3 mg of tetrarhodiumdodecacarbonyl [$Rh_4(CO)_{12}$] were fed into the same quartz cell as that used in Example 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. The rays which were emitted from a 500-W high-pressure mercury lamp set on an irradiation apparatus as an outer light source and passed through a filter UV-25, mfd. by Toshiba Corporation, were used in the irradiation. After the irradiation had been conducted for 10 hours in such a manner, the reaction solution was analyzed by gas chromatography. Cyclooctene was obtained in a yield of 81% with the formation of cyclooctane in a yield of 12%. 7% of unreacted, 1,5-cyclooctadiene remained.

EXAMPLE 8

0.3 ml of 1,5-cyclooctadiene, 32 ml of methanol, 8 ml of acetone and 3 mg of rhodium chloride trihydrate [$RhCl_3 \cdot 3H_2O$] were fed into the same quartz cell as that used in the Example 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. The rays which were emitted from a 500-W high-pressure mercury lamp set on an irradiation apparatus as an outer light source and passed through a filter UV-25, mfd. by Toshiba Corporation, were used in the irradiation. After the irradiation had been conducted for 5.5 hours in such a manner, the reaction solution was analyzed by gas chromatography. Cyclooctene was obtained in a selectivity of 82%.

EXAMPLE 9

0.3 ml of 1,5-cyclooctadiene, 32 ml of 2-propanol, 8 ml of acetone and 2 mg of hexarhodiumhexadecacarbonyl [$Rh_6(CO)_{16}$] were fed into the same quartz cell as that used in the Example 1. Nitrogen gas was bubbled through the contents under stirring for 10 minutes and thereafter, the irradiation of the cell with light was started. The stirring was conducted with a magnetic stirrer. The reaction cell was put in a quartz-window thermostatic chamber to keep the reaction temperature at 20° C. The rays which were emitted from a 500-W high-pressure mercury lamp set on an irradiation apparatus as an outer light source and passed through a filter UV-25, mfd. by Toshiba Corporation, were used in the irradiation. After the irradiation had been conducted for 6 hours in such a manner, the reacton solution was analyzed by gas chromatography. Cyclooctene was obtained in a yield of 69%.

EXAMPLE 10

0.3 ml of 1,5-cyclooctadiene, 32 ml of methanol, 8 ml of acetone and 2 mg of tetrarhodiumdodecacarbonyl [$Rh_4(CO)_{12}$] were fed into the same quartz cell as that used in the Example 1. Nitrogen gas was bubbled through the contents under stirring for 10 minutes and thereafter, the irradiation of the cell with light was started. The stirring was conducted with a magnetic stirrer The rays which were emitted from a 500-W high-pressure mercury lamp set on an irradiation apparatus as an outer light source and passed through a filter UV-25, mfd. by Toshiba Corporation, were used in the irradiation. After the irradiation had been conducted for 5 hours in such a manner, the reaction solution was analyzed by gas chromatography. Cyclooctene was obtained in a yield of 80%.

EXAMPLE 11

0.3 ml of 1,5-cyclooctadiene, 32 ml of ethanol, 8 ml of acetone and 2 mg of tetrarhodiumdodecacarbonyl [$Rh_4(CO)_{12}$] were fed into the same quartz cell as that used in Example 1. Nitrogen gas was bubbled through the contents under stirring for 10 minutes and thereafter, the irradiation of the cell with light was started. The stirring was conducted with a magnetic stirrer. The cell was put in a quartz-window thermostatic chamber to keep the reaction temperature at 20° C. The rays which were emitted from a 500-W high-pressure mercury lamp set on an irradiation apparatus as an outer light source and passed through a filter UV-25, mfd. by Toshiba Corporation, were used in the irradiation. After the irradiation had been conducted for 5 hours in such a manner, the reaction solution was analyzed by gas chromatography. Cyclooctene was obtained in a yield of 94%.

EXAMPLE 12

0.3 ml of 1,5-cyclooctadiene, 32 ml of sec-butanol, 8 ml of acetone and 12 mg of tetrarhodiumdodecacarbonyl [$Rh_4(CO)_{12}$] were fed into the same quartz cell as that used in the Example 1. Nitrogen gas was bubbled though the contents under stirring for 10 minutes and thereafter, the irradiation of the cell with light was started. The stirring was conducted with a magnetic stirrer. The cell was put in a quartz-window thermostatic chamber to keep the reaction temperature at 20° C. The rays which were emitted from a 500-W high-pressure mercury lamp set on an irradiation apparatus as an outer light source and passed through a filter UV-25, mfd. by Toshiba Corporation, were used in the irradiation. After the irradiation had been conducted for 5 hours, the reaction mixture was analyzed by gas chromatography. Cyclooctene was obtained in a yield of 90%.

As described above, cyclooctene can be prepared in a yield as high as 80 to 95% in one step by partially hydrogenating 1,5-cyclooctadiene at ordinary temperature under normal pressure according to the present invention. The cyclooctene prepared according to the present invention can be polymerized in the presence of a catalyst such as $WCl_6$ or an irridium compound through the cleavage of the double bond to give a polymer as represented by the following formula:

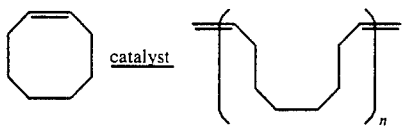

(see e.g., A. Drepeau et al., J. Macromol. Sci. Chem., A20, 986).

Since cyclooctene has a double bond, it is oxidized by oxygen into a dicarboxylic acid having eight carbon atoms through ring opening and this dicarboxylic acid is useful for the preparation of a polymer, such as polyester or polyamide, like adipic acid and so forth.

What is claimed is:

1. A process for the preparation of cyclooctene which comprises irradiating 1,5-cyclooctadiene with an effective amount of ultraviolet light, having a wave length of 400 nm or below, in the effective presence of a photodehydrogenation catalyst, acetone and an alcohol to partially dehydrogenate the 1,5-cyclooctadiene to cyclooctene.

2. A process as set forth in claim 1, wherein said photodehydrogenation catalyst is a rhodium complex.

3. A process as set forth in claim 1, wherein said photodehydrogenation catalyst is a mixture comprising a rhodium complex and a transition metal salt.

4. A process as set forth in claim 1, wherein said alcohol is one selected from among methanol, ethanol, 2-propanol and sec-butanol.

5. A process as claimed is claim 2 wherein said rhodium complex is at least one member selected from the group consisting of $Rh_4(CO)_{12}$, $Rh_6(CO)_6$, and $RhCl_3H_2O$.

6. A process as claimed in claim 3 wherein said rhodium complex is at least one member selected from the group consisting of $Rh_4(CO)_{12}$, $Rh_6(CO)_6$, and $RhCl_3H_2O$.

7. A process as claimed in claim 3 wherein said transition metal salt is a salt of at least one metal selected from the group consisting of iron, cobalt, nickel, copper, and zinc.

8. A process as claimed in claim 3 wherein said transition metal salt is present in an effective amount of 0.05 to 3 moles per mole of said rhodium salt.

9. A process as claimed in claims 2 or 3 wherein said rhodium salt is present in an effective amount of $1 \times 10^{-4}$ to $1 \times 10^{-1}$ mmol per total moles of said alcohol and acetone.

10. A process as claimed in claim 1 wherein the volume ratio of said acetone to said alcohol is 0.05 to 2.

11. A process as claimed in claim 1 wherein said irradiation is from a high pressure mercury vapor lamp.